(12) United States Patent
Hartung (10) Patent No.: US 8,415,647 B2
(45) Date of Patent: Apr. 9, 2013

(54) IRRADIATION APPLIANCE

(75) Inventor: Martin G. Hartung, Gilching (DE)

(73) Assignee: 3M Innovative Properties Company, Saint Paul, MN (US)

( * ) Notice: Subject to any disclaimer, the term of this patent is extended or adjusted under 35 U.S.C. 154(b) by 129 days.

(21) Appl. No.: 12/909,575

(22) Filed: Oct. 21, 2010

(65) Prior Publication Data

US 2011/0033816 A1    Feb. 10, 2011

Related U.S. Application Data

(63) Continuation of application No. 10/514,034, filed as application No. PCT/EP03/05316 on May 21, 2003, now abandoned.

(30) Foreign Application Priority Data

May 21, 2002   (DE) .................................. 10222828

(51) Int. Cl.
*G02B 1/00* (2006.01)
*G02B 5/00* (2006.01)
(52) U.S. Cl. ............... 250/504 H; 368/105; 600/247; 600/248; 433/29; 433/30; 433/31; 250/455.11
(58) Field of Classification Search ............ 250/455.11, 250/504 H; 368/105; 600/247–248
See application file for complete search history.

(56) References Cited

U.S. PATENT DOCUMENTS

| | | |
|---|---|---|
| 3,645,771 A | 2/1972 | Ward |
| 4,185,891 A | 1/1980 | Kaestner |
| 4,836,782 A | 6/1989 | Gonser |
| 4,839,566 A | 6/1989 | Herold et al. |
| 5,001,609 A | 3/1991 | Gardner et al. |
| 5,063,255 A | 11/1991 | Hasegawa et al. |
| 5,249,862 A | 10/1993 | Herold et al. |
| 5,371,826 A | 12/1994 | Friedman |
| 5,420,768 A | 5/1995 | Kennedy |
| 5,487,662 A | 1/1996 | Kipke et al. |
| 5,534,772 A | 7/1996 | Rogers |
| 5,634,711 A | 6/1997 | Kayser |
| 5,702,250 A | 12/1997 | Kipke |
| 5,803,729 A | 9/1998 | Tsimerman |
| 6,095,812 A | 8/2000 | Senn et al. |

(Continued)

FOREIGN PATENT DOCUMENTS

| | | |
|---|---|---|
| DE | 1040875 | 10/1958 |
| DE | 34 00 781 | 7/1985 |

(Continued)

OTHER PUBLICATIONS

R. Worthington, "Acceptance—Angle Measurement of Multimode Fibers: A comparison of Techniques," Oct. 1, 1982, Applied Optics, vol. 21, No. 19, pp. 3515-3519.

(Continued)

*Primary Examiner* — Jack Berman
*Assistant Examiner* — Meenakshi Sahu
(74) *Attorney, Agent, or Firm* — Carlos M. Téllez (57) ABSTRACT

The invention relates to a radiation device that includes a housing, a light-emitting unit and a light-absorbing unit which is provided with an inlet opening and a reflector element. The reflector element extends across the entire distance between the light-emitting unit and the inlet opening of the light-absorbing unit.

25 Claims, 3 Drawing Sheets

U.S. PATENT DOCUMENTS

| | | | |
|---|---|---|---|
| 6,123,545 | A | 9/2000 | Eggler et al. |
| 6,129,450 | A | 10/2000 | Braun |
| 6,157,141 | A * | 12/2000 | Lapatovich et al. ........... 315/248 |
| 6,159,005 | A * | 12/2000 | Herold et al. .................... 433/29 |
| 6,200,134 | B1 | 3/2001 | Kovac et al. |
| 6,256,067 | B1 | 7/2001 | Yamada |
| 6,318,996 | B1 | 11/2001 | Melikechi et al. |
| 6,345,982 | B1 | 2/2002 | Meyer |
| 6,406,293 | B1 * | 6/2002 | Burstein ......................... 433/29 |
| 6,419,483 | B1 | 7/2002 | Adam et al. |
| 6,500,001 | B2 | 12/2002 | Horth et al. |
| 6,692,251 | B1 * | 2/2004 | Logan et al. .................... 433/29 |
| 6,724,522 | B2 | 4/2004 | Hartung |
| 6,857,873 | B2 * | 2/2005 | Bianchetti et al. .............. 433/29 |
| 6,932,599 | B1 | 8/2005 | Hartung |
| 6,971,876 | B2 | 12/2005 | Cao |
| 7,077,649 | B2 | 7/2006 | Bretscher et al. |
| 7,153,015 | B2 | 12/2006 | Brukilacchio |
| 7,182,597 | B2 | 2/2007 | Gill et al. |
| 2002/0064754 | A1 | 5/2002 | Horth et al. |
| 2002/0168605 | A1 * | 11/2002 | Cao ................................. 433/29 |
| 2003/0036031 | A1 * | 2/2003 | Lieb et al. ....................... 433/29 |
| 2003/0218880 | A1 | 11/2003 | Brukilacchio |
| 2004/0038173 | A1 | 2/2004 | Brandhorst et al. |
| 2005/0236586 | A1 | 10/2005 | Hartung |

FOREIGN PATENT DOCUMENTS

| | | |
|---|---|---|
| DE | 298 00 633 | 6/1999 |
| DE | 19 801 531 | 7/1999 |
| DE | 298 21 809 | 5/2000 |
| DE | 19 903 753 | 10/2000 |
| EP | 0 422 413 | 4/1991 |
| EP | 0 755 665 | 1/1997 |
| EP | 0 879 582 | 11/1998 |
| HU | 27343 T | 10/1983 |
| JP | S57-156230 | 10/1982 |
| JP | 7-163593 | 6/1995 |
| JP | 08-141001 | 6/1996 |
| JP | 113526 | 6/1996 |
| JP | 9-010238 | 1/1997 |
| JP | 190908 | 4/1997 |
| JP | 9-122153 | 5/1997 |
| WO | WO 96/00560 | 1/1996 |
| WO | WO 97/36552 | 10/1997 |
| WO | WO 98/43727 | 10/1998 |
| WO | WO 99/16136 | 4/1999 |
| WO | WO 00/13608 | 3/2000 |
| WO | WO 00/77446 | 12/2000 |
| WO | WO 01/19280 | 3/2001 |
| WO | WO 01/64129 | 9/2001 |
| WO | WO 02/11640 | 2/2002 |
| WO | WO 2004/045445 | 6/2004 |

OTHER PUBLICATIONS

"Lumen Maintenance of White Luxeon™ Power Light Sources," Lumiledgs, Publication No. AB07, May 2002.

* cited by examiner

IRRADIATION APPLIANCE

CROSS-REFERENCE TO RELATED APPLICATIONS

The present application is a continuation of U.S. patent application Ser. No. 10/514,034, filed Apr. 29, 2005, now abandoned which is a U.S. National Stage Application of PCT/EP2003/005316, filed May 21, 2003, which claims priority from German Application No. 10222828.0, filed May 21, 2002.

BACKGROUND AND SUMMARY OF THE INVENTION

JP 9-10238 A discloses a dental irradiation appliance, in which an array composed of light-emitting diodes is arranged on the cap surface of an optically conductive body which is in the form of a spherical sector and is composed of quartz or plastic, and whose tip merges into an optical waveguide rod. The beams from the light-emitting diodes are focused by the optically conductive body by reflection on the conical wall, and are introduced into the optical waveguide rod.

WO-97/36552 A discloses a further dental irradiation appliance, in which a planar array composed of light-emitting diodes with parallel optical axes is opposite the curved inlet surface of an optically conductive body, which is once again conical. This condenser is coupled on the output side to an optical waveguide, and may be filled with an optically transparent liquid.

Apart from the fact that conical optically conducting bodies such as these and as described in the documents cited above, or else as described in WO 99/16136 (FIG. 4), are complex to manufacture and increase the weight of the appliance, they also cause considerable radiation losses. This is because, whenever a light beam is reflected on the conical wall of the optically conductive body, the beam is deflected through twice the cone angle from the optical axis. Even after a small number of reflections, this leads to the angle for total internal reflection in the optical waveguide being exceeded, and in the beams emerging from the optical waveguide, or, if the optical waveguide is mirrored, even in the direction of the beams being rotated, and thus not being passed to the light outlet opening, but being passed back to the light inlet opening.

Arrangements such as these thus function only for that component of the light injected from the LEDs whose beams are tilted only in a very narrow angle range with respect to the optical axis. The majority of the light emitted from the LEDs can thus not be used to illuminate the treatment area, since the light cones with which LEDs emit light normally have a considerably greater aperture angle.

WO-99/16136 A (FIG. 6) also discloses an appliance having a multiple-conical optically conductive body, in which two or more annular light inlet areas precede a circular light inlet area. In this case, the light is guided by the multiple-conical optically conductive body from the first circular light inlet area into the central area between the first annular light inlet area. Together with the light from the LEDs, which irradiate this light inlet opening arranged in an annular shape, it is now passed into the center of a further combination of an LED ring and an annular inlet area. The light gathered in this way is now passed to an outlet opening through the optical waveguide, whose further profile is once again conical.

In this arrangement as well, and for the reasons mentioned above, only a small proportion of the beams which are emitted from the LEDs reach the light outlet opening, and hence the point to be irradiated. As a result of two or more conical optically conducting bodies being arranged one behind the other, the efficiency of the areas which are located furthest away from the outlet opening is reduced even further than that in the case of a single-conical condenser. Furthermore, it is even more difficult and expensive to manufacture the multiple-conical optical waveguide.

Other embodiments of irradiation appliances which are based on LEDs and manage without a conical optically conductive body, and hence without the disadvantages associated with them, are also known. For example, JP 08-141001 A (FIG. 1) and WO-99/35995 A (FIG. 4) propose optical convergent lenses for focusing the beams emitted from an LED array, and for focusing them onto the light inlet area of an optical waveguide.

In this case, all of the beams which are emitted from the individual LEDs in the direction of the convergent lens are deflected. However, the deflection to the desired direction and the focusing of the beams once again take place only for that proportion of the beams which strike the convergent lens essentially parallel, or differ slightly from this direction depending on the size of the light inlet area. A considerable proportion of the beams cannot be passed from the convergent lens to the light inlet opening, and this proportion is thus lost for the irradiation of the treatment point.

In the arrangement which is illustrated in FIG. 1 of WO-99/35995 A, 9 LEDs are aligned individually in the direction of one optical waveguide, in which case it has been possible to observe only partial hardening of a light-hardening sample. This is a result of inadequate light power as a consequence of non-optimum light injection, as well as the small number of LEDs which can be used with the described arrangement.

In a further appliance, which is described in WO-00/13608 A, and is based on a similar arrangement of the LEDs with respect to the light inlet opening of an optical waveguide, the light power is increased firstly by using a conical optical waveguide, and secondly by applying a multiple of the nominal operating current to the diodes. The conical optical waveguide results in the problems which have already been described further above.

The high operating currents have the disadvantage that the heat losses in the LEDs increase more than proportionally and are large, so that the appliance becomes warm after a short time, and cannot be used for a lengthy time, until it has cooled down. Furthermore, the life of LEDs is greatly decreased by the high operating currents. This is evident from a continuous decrease in the light power over the course of time.

The arrangements of LEDs in the form of individual semiconductor chips, as proposed in WO-99/35995 A, WO 02/11640 A2 or EP 0 879 582 A, on a common substrate are not without their problems either, since the individual elements heat one another up, thus once again limiting the light intensity and/or the life. Furthermore, it is considerably more complex and expensive to produce arrangements such as these, since it is not possible to use standard components, which are also mechanically easy to handle.

A further irradiation appliance having two or more LEDs is disclosed in WO-01/19280 A. The LEDS are arranged in a specific manner on a number of levels in order to allow the light that is produced to be injected as advantageously as possible into an optical waveguide.

All of the above appliances have the common feature that the achievable light powers are limited by the LED arrangements described there.

In order to further increase the light power, an array comprising a large number of individual LEDs is proposed. However, as the number of individual LEDs increases, it becomes ever more difficult to gather their emitted light. By way of example, WO 02/11640 A2 discloses a focusing lens in addition to a reflector, in order to focus the beams from the LED array in order that they can be injected into an optical waveguide.

Furthermore, as the number of LEDs rises, the space required, the electrical power required and the electrical heat losses which have to be dissipated from the LEDs in order to allow a long life also increase. For the reasons stated, it would be desirable to manage as far as possible with only one individual LED, and this would have a positive influence on the production costs.

In principle, it is possible to use high-power LEDs to achieve this object, which can emit far greater light power levels than conventional LEDs. However, the light that is produced must be gathered with as few losses as possible in this case as well and, for example, must be passed by means of an optical waveguide to the treatment point, since the performance of an LED array can otherwise not be achieved.

Irradiation appliances which are equipped with only one LED have been proposed, for example, in the documents U.S. Pat. No. 6,318,996 B1 and WO 01/64129 A1. WO 01/64129 proposes that such high currents be applied to the LED that the life is shorter than 10 hours since, otherwise, it is not possible to achieve sufficient radiation power.

In U.S. Pat. No. 6,318,996, an intensity of only between 25 and about 38 mW/cm$^2$ is achieved with a single LED. Values such as these are relatively low for irradiation appliances for hardening dental materials. This is accordingly also based on a relatively long illumination time of 60 seconds. Furthermore, the LED should be positioned at a distance of 7 mm±2 mm from the material to be hardened. This means that the LED is located in the patient's mouth. Even if the LED is encapsulated in a housing, adequate hygiene is impossible, as is normally achieved by means of sterilization at temperatures of about 130° C., since these high temperatures could destroy the LED. For this reason, optically conducting elements such as fiber-optical waveguides have been introduced as standard for irradiation appliances for hardening dental materials. These can be removed from the housing, and sterilized, after the treatment.

It has been found that light beams can be injected into a fiber-optical waveguide largely without losses only when they strike the inlet area at a specific angle, which is less than or equal to the so-called acceptance angle.

This acceptance angle is typically ±30°. The possible LEDs emit light, however, in a cone whose aperture angle is in some circumstances greater than this maximum injection angle. Only some of the power can therefore be used when the LED is arranged directly in front of the optical waveguide.

However, owing to the wide aperture angle of LEDs (for example ±50° or more), lenses are suitable only to a restricted extent for increasing the injection efficiency. Although such lenses can be used to deflect and inject some of the beams whose angles are greater than the acceptance angle, at the same time, however, the efficiency of the injection process for the beams which could intrinsically be injected directly falls, for example, as a result of reflection losses, since these beams also have to pass through the lens.

Direct injection of the beams which are emitted within the acceptance angle of, for example, the LED, that is to say without having previously been focused by refractive or reflective optical elements, would be particularly advantageous since there would then be no need to accept any losses whatsoever as a result of radiation refraction or focusing.

On the other hand, optical elements are required in order to make it possible to use the beams emitted outside the acceptance angle, as well.

In summary, all known embodiments of high-power light appliances use complex arrangements of a greater or lesser number of light-emitting elements in order to achieve intensities which are as high as possible. The greater the number of individual elements in this case, the more complex and at the same time the more lossy the required optical elements or arrangements which are necessary in order to gather and focus the light from the individual elements. However, if only a small number of light-emitting elements, or only one light-emitting element, are or is used, then either the radiation power is low or other serious disadvantages must be accepted, such as lack of hygiene or short life.

In consequence, one object of the present invention is to provide an irradiation appliance having as few light-emitting units as possible, which is simple to manufacture but has a light power which is comparable to or better than that of appliances with LED arrays.

A further object is to provide an irradiation appliance by means of which light-hardening dental filling materials can be hardened more quickly and reliably.

Finally, the reduction in the space that is required for the light-emitting unit and the rechargeable battery that is required is intended to reduce the size of the appliance, not least making it possible to reduce the production costs.

Furthermore, the light-emitting unit should have a long life. Simple cleaning of the appliance is also desirable, as can be achieved with normal optical waveguides.

This object is achieved by an irradiation appliance as is described in the claims.

The expressions "contain" and "comprise" for the purposes of the invention introduce a non-exclusive enumeration of features. Similarly, the expression "a or one" should be understood in the sense of "at least one".

It has been found that higher efficiency and a higher radiation yield with reduced complexity and less space being required can be achieved by the provision or installation of a reflector element which is arranged as selective combining optics between a light-emitting and light-receiving unit.

This takes account of the fact that a considerable proportion of the light from, for example, one LED is emitted such that it can be injected directly into an optical waveguide. These beams are not intended to be influenced by the selective combining optics or the reflector element, since this would generally be associated with attenuation. Only those beams whose tilt angle with respect to the optical axis is greater than the acceptance angle are intended to be deflected in this way and deflected in the direction of the opening in the optical waveguide, such that they can be injected.

It has been found that neither the directly injected beams nor the deflected beams allow satisfactory light conduction. Adequate performance of the irradiation appliance is guaranteed only by optimum use of both components in total, as is possible by means of the arrangement according to the invention.

The reflector element extends over the entire distance from the emission surface of the light-emitting element to the inlet surface of the light-receiving element. The expression "the entire distance" does not, however, mean that there must be no variation whatsoever between the reflector element and the light-receiving element, as may be caused, for example, by design and manufacturing factors. However, in any case, the variation should be minimized.

This includes any variation caused by manufacturing or design in the transition from the outlet surface of the reflector element to the inlet surface of the light-receiving element which, for example, allows the attachment or fitting of an optical waveguide. A small gap is also possible between the outlet surface of the reflector element and the inlet area of the light-receiving unit, into which a thin glass panel is introduced. This is used to protect the sensitive reflector surface against dirt. The glass panel ideally has optical blooming on both sides in order to avoid radiation losses resulting from reflections.

A suitable reflector element has, for example, a conical shape and is hollow internally, that is to say it is not filled with a refractive medium in the optical sense.

The reflector element is preferably in the form of a truncated conical surface which faces at least the light-emitting element and is mirrored on the inside. The smaller cross-sectional area of the cone in this case faces the light-emitting unit.

The light-emitting unit is arranged at a distance in front of the light-receiving element such that the proportion of the light beams which can be injected directly (that is to say light beams at angles less than or equal to the acceptance angle) completely illuminates the inlet area.

This represents the optimum arrangement for this proportion of the light cone, since, in this case, no losses occur as a result of refraction, diffraction or boundary surface transitions at any optical elements whatsoever. In the case of fiber-optical waveguides, this generally means that the distance to the light-emitting unit is somewhat greater than or equal to half the diameter of the inlet opening of the light-receiving unit.

The truncated conical surface which is defined by this arrangement between the light-emitting unit and the light-receiving element is thus, according to the invention, bounded by a reflector element. This reflector element opens from the diameter of the light-emitting unit to that of the light-receiving unit, so that the angle of the cone is defined by the distance from the light-emitting unit to the light-receiving unit.

By adaptation of the cross section of the inlet opening of the light-receiving unit, it is thus possible to achieve specific angles in order to select an optimum arrangement for the respective embodiment of the light-emitting unit.

All beams which have an emission angle that is greater than the acceptance angle strike the reflector element, where they are reflected, with the angle with respect to the optical axis now being reduced by twice the reflector element angle.

If, for example, a light beam at an angle of 50° with respect to the optical axis strikes the reflector element with an opening angle of 10°, then, after reflection, its angle is −30°, this being the angle at which it strikes the optical waveguide, and can now be injected.

The reflector element preferably has the following features for this purpose:

The inlet opening of the reflector element is sufficiently large that all of the beams which are emitted from the light-emitting unit can be received, that is to say it is generally of the same size as the LED lens that is used.

The outlet opening of the reflector element has approximately the same diameter as the inlet opening of the light-receiving element.

The aperture angle of the reflector element follows the relationship: inclination angle=0.5×(maximum beam angle−acceptance angle).

In addition, the inclination angle can also decrease from higher values at the start (close to the light-emitting unit) to smaller values, since the beams which are reflected at the start have a higher tilt angle than those close to the optical waveguide.

The maximum beam angle is predetermined by the emission characteristic of the light-emitting unit and characterizes the beams which are still intended to be used for irradiation of the treatment point. Beams with an even greater angle are either not emitted or are emitted only with a negligible intensity from the light-emitting element, so that their use would not contribute to significantly increasing the intensity.

By way of example, commercially available high-power diodes emit 30% of the total intensity within the acceptance angle of normal optical waveguides of ±30°, a further 60% in an angle range between 30° and 50°, and the remaining 10% at emission angles between 50° and 90°. Since their use would produce a small amount comparable to the 30° to 50° range, the maximum beam angle is sensibly set at 50° in this example.

The maximum beam angle may thus, for example, be about 65°, preferably about 55°, and particularly preferably about 50°.

The light-emitting units which are used preferably have a life of many hundred hours, and preferably more than 1000 hours, emit in a range from 400 to 500 nm, have an emission maximum between 440 and 480 nm and have a light power of at least 100 mW, preferably at least 200 mW.

The irradiation appliance is distinguished, inter alia, by the following features:

It preferably has only one reflector element and has no further combining optics, which operate in a reflective or refractive manner, in the area between the light-emitting unit and the inlet opening of the light-receiving unit.

It preferably has no active cooling elements operated by means of electrical power.

It can preferably be operated independently of the mains system.

A polished metal body composed, for example, of aluminum, titanium or stainless steel may be used as the reflector element material, as well as metal sheets with good reflection characteristics, mirroring layers or else, for example, metal-free interference mirror sheets such as those known from WO 00/07044 and available, for example, from 3M.

For the purposes of the invention, a light-emitting unit is any compact form of radiation source which produces light, preferably at a wavelength in the range from 400 to 500 nm. This emission is preferably directional and can be achieved by means of optical elements which are integrated in the light-emitting unit, such as those normally used for high-power light-emitting diodes. The internal configuration of the unit is in this case irrelevant, irrespective of whether it comprises a single light-emitting element, or a combination of two or more light-emitting elements.

In particular, the term light-emitting unit includes light-emitting diodes (LEDs). However, it is also possible to use laser diodes, such as those described in EP 0 755 662 A.

A light-receiving unit for the purposes of the invention is any apparatus which has the capability to receive and to re-emit directionally light which is produced by the light-emitting unit or the light-emitting elements.

These are normally so-called optical waveguide rods, which comprise a large number of bundled glass fibers. These optical waveguide rods can be reversibly connected to the light-emitting unit, or to the housing which contains it, via a coupling or a thread.

However, this also includes conventional filter disks, scattered-light disks or optical waveguide converters, such as those described in DE 100 06 286 C1.

If required, the light-emitting unit and/or the reflector element is/are covered with a transparent disk, in order to protect the light-emitting unit and/or the reflector element against moisture and dirt when the optical waveguides are removed.

The light-emitting unit is preferably mounted on a normally flat panel.

The problem of dissipating the heat which is produced by the light-emitting element during operation of the irradiation appliance can be solved by the use of thermally highly conductive board material and/or direct thermally conductive attachment of the element to a heat sink. The heat is in this case passed to the appliance housing by thermal conduction, from where it is radiated away to the environment. There is therefore no need to use active cooling elements, such as fans or Peltier elements, which consume additional power and, in the case of a fan, produce a high noise level. Furthermore, a further improvement in hygiene is achieved, since no ventilation slots need be provided, since these are difficult to keep clean.

In order to entrap the amount of heat that is produced during normal short-term operation, and thus to keep the temperature of the light-emitting unit low, which lengthens the life, an additional element with a high thermal capacity can be thermally connected to the light-emitting unit. This stores the amount of heat produced during operation, and emits it continuously to the environment via the thermally highly conductive housing during pauses in treatment.

The irradiation appliance normally also has an electronic control unit for controlling the voltage and current level for the light-emitting element, a storage unit for electrical energy, such as batteries or rechargeable batteries, preferably lithium-ion, NiMH or Ni/Cd rechargeable batteries, a display unit and a housing.

The housing is preferably designed such that it essentially has a surface without any gaps, in which the display unit is integrated.

The illumination appliance according to the invention is used in particular in the medical field, preferably in the dental field, and may on the one hand be used to illuminate the treatment point or to irradiate substances which can be cured by light, in particular dental filling materials, such as composites, compomers or glass ionomer cements.

During use, the outlet end of the optical waveguide rod is pointed at the treatment point, for example at a tooth filling to be hardened, and the switch-on pushbutton is pressed, thus activating the LED and at the same time switching on the display unit. After a predetermined or variable time interval, the control circuit switches off the power supply to the light-emitting diode and to the display unit.

In one embodiment, the irradiation appliance has a reflector element wherein the length of the reflector element may be greater than the distance between the light-emitting unit and the light-receiving unit. The reflector element may be a truncated cone which may be reflective on the inside and the larger opening in the reflector element may be covered by an optical protective glass. The inner surface of the truncated cone may be metallically mirrored or may be formed from a sheet with high optical reflection. The sheet may be a metal-free, multilayer interference reflector sheet. The light-emitting unit may be a blue high-power light-emitting diode, with at least one light-emitting element whose size may be at least 0.25 $mm^2$, and the unit may produce a radiation power between 100 and 1400 mW. Alternatively, the at least one light-emitting element size may be between 1 and 5 $mm^2$, and the radiation power between 200 and 800 mW. The housing of the irradiation appliance may be composed entirely or partially of a material of high thermal conductivity and thermal capacity and the housing may be composed entirely or partially of aluminum, zinc or brass. The light-emitting unit may also be thermally connected to an element having a thermal capacity between 10 and 100 Joule/Kelvin, or preferably between 20 and 50 Joule/Kelvin. The light-receiving element may be selected from a rigid optical waveguide rod or a flexible optical waveguide.

In another embodiment, the reflector element may selectively deflect only those light beams whose emission angel from the light-emitting unit is greater than the acceptance angel of the light-receiving unit in a desired inlet angle range into the light-receiving unit, but may leave other light beams unaffected.

Preferred exemplary embodiments will be explained in the following text with reference to the drawings, in which.

BRIEF DESCRIPTION OF THE DRAWINGS

DETAILED DESCRIPTION OF THE INVENTION

Figure 1:
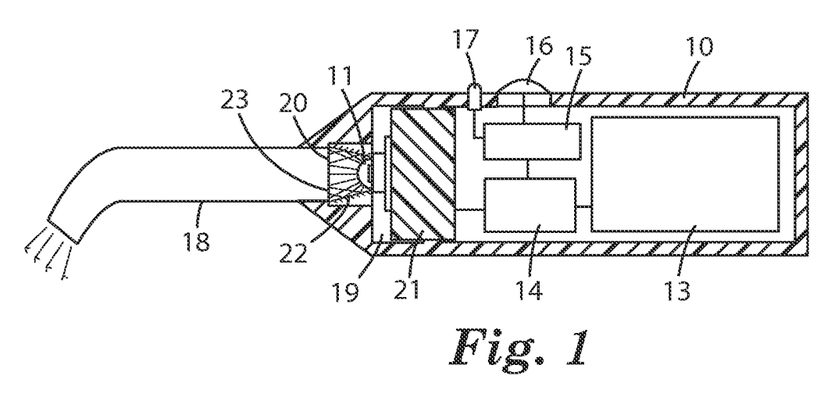
FIG. 1 shows a longitudinal section through an irradiation appliance.

The handheld appliance shown in FIG. 1 for irradiation of dental plastics contains a light-emitting unit (11), with a light-emitting element in the form of an LED chip (12), in the front area of an essentially cylindrical housing (10).

The light-emitting element (12) is fed from a battery (13), which is arranged in the rear part of the housing (10), via a driver stage (14) which is time-controlled by a control circuit (15). The control circuit (15) is connected to a switch-on pushbutton (16), which is arranged on the side of the housing (10), and to a display diode (17), which is likewise arranged on the side of the housing (10). A light-receiving unit (18) in the form of an optical waveguide rod, whose front end is curved, projects out of the front conical end of the housing (10). The light-emitting element (12) is located on a flat holding plate (19).

Figure 2:
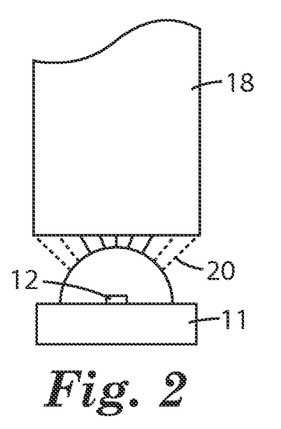
FIG. 2 shows a longitudinal section through an irradiation appliance in the area of the transition from the light-emitting element to the light-receiving element, without a reflector element.

FIG. 2 shows which of the beams which are emitted from the light-emitting element (12) can be injected, for example, into an optical waveguide (18), and which cannot. The beams which are symbolized by a solid line can be injected into the optical waveguide while, in contrast, the beams illustrated by dashed lines cannot be injected into it, since their angle with respect to the optical axis is greater than the acceptance angle of the optical waveguide.

Figure 3:
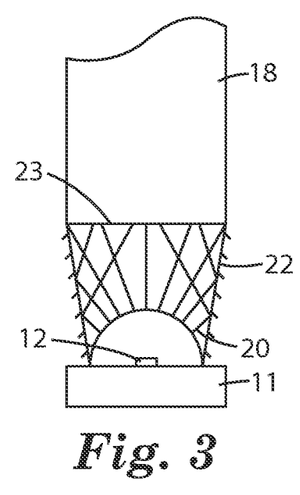
FIG. 3 shows a longitudinal section corresponding to that shown in FIG. 1, with a reflector element in the form of a cone.

FIG. 3 corresponds essentially to FIG. 2, with the difference that a reflector element (22) in the form of a mirrored truncated conical surface extends from the surface of the light-emitting unit (12) to the inlet surface of the optical waveguide (18). By virtue of this reflector element, those beams which otherwise cannot be injected into the optical waveguide because of their angle, which is greater than the acceptance angle of the optical waveguide, can also, however, in the end be injected, since the magnitude of their tilt angle with respect to the optical axis is reduced by twice the reflector aperture angle, as a consequence of reflection. Those beams which are emitted from the light-emitting unit within a light cone with angles less than the acceptance angle directly illuminate the inlet opening of the optical waveguide, so that their intensity can be made use of as well as possible.

List of Reference Symbols:

| | |
|---|---|
| 10 | Housing |
| 11 | Light-emitting unit |
| 12 | Light-emitting element/light-emitting diode |
| 13 | Battery |
| 14 | Driver stage |
| 15 | Control circuit |
| 16 | Switch-on pushbutton |
| 17 | Display unit |
| 18 | Light-receiving unit/optical waveguide rod |
| 19 | Holding plate |
| 20 | Focus range |
| 21 | Heat sink body |
| 22 | Reflector element |
| 23 | Optical protective glass |

The invention claimed is:

1. An irradiation appliance, having:
a housing;
a single light-emitting unit which is arranged in the housing;
a light-receiving unit comprising an optical wave guide and having an inlet opening; and
a reflector element having an inner surface in the shape of a truncated cone,
wherein the reflector element extends over the entire distance between the light-emitting unit and the inlet opening of the light-receiving unit and has a smaller and a larger opening;
wherein the smaller opening faces the light-emitting unit, and the larger opening faces the light-receiving unit; and
wherein the reflector element has an aperture angle that decreases in size from the smaller opening to the larger opening.

2. The irradiation appliance as claimed in claim 1, wherein the larger opening has a diameter that is less than or equal to that of the light-receiving unit.

3. The irradiation appliance as claimed in claim 1, wherein the smaller opening at least partially surrounds the light-emitting unit.

4. The irradiation appliance as claimed in claim 1, wherein the distance between the light-emitting unit and the light-receiving unit is greater than half the diameter of the light-receiving unit.

5. The irradiation appliance as claimed in claim 1, wherein the length of the reflector element is greater than the distance between the light-emitting unit and the light-receiving unit.

6. The irradiation appliance as claimed in claim 1, wherein the larger opening in the reflector element is covered by an optical protective glass.

7. The irradiation appliance as claimed in claim 6, wherein the optical protective glass has blooming on one or both faces.

8. The irradiation appliance as claimed in claim 1, wherein the reflector element is reflective on the inside.

9. The irradiation appliance as claimed in claim 8, wherein the inner surface of the truncated cone is metallically mirrored or is formed from a sheet with high optical reflection.

10. The irradiation appliance as claimed in claim 9, wherein the sheet is composed of a metal with good reflection characteristics, or is coated with such a metal.

11. The irradiation appliance as claimed in claim 9, wherein the sheet is a metal-free, multilayer interference reflector sheet.

12. The irradiation appliance as claimed in claim 1, wherein the light-emitting unit is a blue high-power light-emitting diode, comprising at least one light-emitting element whose size is at least 0.25 mm$^2$, and the unit produces a radiation power between 100 and 1400 mW.

13. The irradiation appliance as claimed in claim 12, wherein the at least one light-emitting element size is between 1 and 5 mm$^2$, and the radiation power is between 200 and 800 mW.

14. The irradiation appliance as claimed in claim 1, wherein the light-emitting unit is thermally connected to the housing.

15. The irradiation appliance as claimed in claim 14, wherein the housing is composed entirely or partially of a material of high thermal conductivity and thermal capacity.

16. The irradiation appliance as claimed in claim 15, wherein the housing is composed entirely or partially of aluminum, zinc or brass.

17. The irradiation appliance as claimed in claim 15, wherein the light-emitting unit is additionally thermally connected to an element having a thermal capacity between 10 and 100 Joule/Kelvin.

18. The irradiation appliance as claimed in claim 17, wherein the thermal capacity is between 20 and 50 Joule/Kelvin.

19. The irradiation appliance as claimed in claim 1, wherein the light-emitting element is mounted on a planar holding plate of high thermal conductivity.

20. The irradiation appliance as claimed in claim 1, wherein the light-receiving element is selected from a rigid optical waveguide rod or a flexible optical waveguide.

21. An irradiation appliance, having:
a housing;
a single light-emitting unit which is arranged in the housing;
a light-receiving unit comprising an optical wave guide and having an inlet opening; and
a reflector element which extends over the entire distance between the light-emitting unit and the inlet opening of the light-receiving unit and has a smaller and a larger opening, and an inclination angle v;
wherein the smaller opening faces the light-emitting unit, and the larger opening faces the light-receiving unit; and
wherein the inclination angle v of the reflector element follows the relationship:

$v = 0.5 \times (\delta - \alpha)$ where $\delta$ is a maximum emission angle at which light beams intended to be injected into the optical waveguide leave the light-emitting unit, and $\alpha$ is an acceptance angle of the optical waveguide.

22. The irradiation appliance as claimed in claim 21, wherein $\delta$ is less than or equal to 65°.

23. The irradiation appliance as claimed in claim 1, wherein the reflector element deflects only light beams emitted from the light-emitting unit that have an emission angle that is greater than a maximum injection angle of the light receiving unit.

24. The irradiation appliance as claimed in claim 23, wherein the maximum injection angle of the light receiving unit is ±30°.

25. The irradiation appliance as claimed in claim 1, wherein light beams having an emission angle less than or equal to the maximum injection angle of the light-receiving unit completely illuminate the inlet opening of the light-receiving unit.

* * * * *

UNITED STATES PATENT AND TRADEMARK OFFICE
CERTIFICATE OF CORRECTION

PATENT NO. : 8,415,647 B2
APPLICATION NO. : 12/909575
DATED : April 9, 2013
INVENTOR(S) : Martin Hartung It is certified that error appears in the above-identified patent and that said Letters Patent is hereby corrected as shown below:

On Title Page 2, Column 2 Item (56) (Foreign Patent Documents)
Line 10    Delete "JP  113526  6/1996" and insert -- JP  113526  8/1996 --, therefor.

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,415,647 B2  
APPLICATION NO. : 12/909575  
DATED : April 9, 2013  
INVENTOR(S) : Martin Hartung It is certified that error appears in the above-identified patent and that said Letters Patent is hereby corrected as shown below:

On the Title Page  
(73) Assignee: Delete "3M Innovative Properties Company, Saint Paul, MN (US)" and insert -- 3M Deutschland GmbH, Neuss, Germany (DE) --, therefor.

Signed and Sealed this  
Thirtieth Day of June, 2015

Michelle K. Lee  
*Director of the United States Patent and Trademark Office*

UNITED STATES PATENT AND TRADEMARK OFFICE
CERTIFICATE OF CORRECTION

PATENT NO. : 8,415,647 B2  
APPLICATION NO. : 12/909575  
DATED : April 9, 2013  
INVENTOR(S) : Hartung Page 1 of 1

It is certified that error appears in the above-identified patent and that said Letters Patent is hereby corrected as shown below:

-- The certificate which issued on June 30, 2015 is vacated because petition to correct assignee under 3.81(b) was not granted by the Office of Petitions. The Certificate of Correction which issued on June 30, 2015 was published in error and should not have been issued for this patent. The assignee is reinstated on the title page of patent at Item (73) as –3M Innovative Properties Company, Saint Paul, MN (US) --.

Signed and Sealed this  
Fourth Day of August, 2015

Michelle K. Lee  
*Director of the United States Patent and Trademark Office*